(12) United States Patent
Joshi

(10) Patent No.: US 11,864,912 B2
(45) Date of Patent: Jan. 9, 2024

(54) DEVICE FOR THE DETECTION AND RELIABLE CAPTURING OF THE PULSE CHARACTERISTICS

(71) Applicant: ATREYA INNOVATIONS PRIVATE LIMITED, Pune (IN)

(72) Inventor: Aniruddha Jyeshtharaj Joshi, Mumbai (IN)

(73) Assignee: ATREYA INNOVATIONS PRIVATE LIMITED, Pune (IN)

( * ) Notice: Subject to any disclaimer, the term of this patent is extended or adjusted under 35 U.S.C. 154(b) by 331 days.

(21) Appl. No.: 16/306,504

(22) PCT Filed: Jun. 1, 2017

(86) PCT No.: PCT/IN2017/050217
§ 371 (c)(1),
(2) Date: Nov. 30, 2018

(87) PCT Pub. No.: WO2017/208261
PCT Pub. Date: Dec. 7, 2017

(65) Prior Publication Data
US 2019/0159726 A1 May 30, 2019

(30) Foreign Application Priority Data
Jun. 3, 2016 (IN) ............... 20162101945

(51) Int. Cl.
*A61B 5/00* (2006.01)
*A61B 5/0205* (2006.01)
*A61B 5/024* (2006.01)

(52) U.S. Cl.
CPC ........ *A61B 5/4854* (2013.01); *A61B 5/02055* (2013.01); *A61B 5/02444* (2013.01); *A61B 5/702* (2013.01); *A61B 5/721* (2013.01)

(58) Field of Classification Search
CPC .............. A61B 5/4854; A61B 5/02055; A61B 5/02444; A61B 5/721; A61B 5/702;
(Continued)

(56) References Cited

U.S. PATENT DOCUMENTS 6,210,340 B1 * 4/2001 Amano .............. A61B 5/02427
600/485
6,364,842 B1 4/2002 Amano et al.
(Continued)

FOREIGN PATENT DOCUMENTS

| CN | 202365775 U | 8/2012 |
| CN | 103153175 A | 6/2013 |

(Continued)

OTHER PUBLICATIONS

Chen et al., "A Non-Contact Pulse Automatic Positioning Measurement System for Traditional Chinese Medicine," Sensors (Basel), vol. 15, No. 5, pp. 9899-9914 (May 2015, published Online Apr. 2015).

(Continued)

*Primary Examiner* — Devin B Henson
(74) *Attorney, Agent, or Firm* — Clark & Brody LP

(57) ABSTRACT

The invention is related to a device to sense the pulse on a wrist of a subject and to arrive at the health status of the said subject by capturing the pulse in real time; analyzing the pulse based on time-frequency properties of the pulse signal and Vata, Pitta and Kaphahumors of the subject. The device reliably detects and captures noise free pulse characteristics of a subject at the appropriate locations of the subject's wrist with minimal positional error in a user friendly way with minimal reliance on the expertise of the person measuring the pulses. The device facilitates the analysis of the pulses and provides a comprehensive diagnostic system based on the pulse characteristics, visual features, responses of a (Continued)

Process of the pulse acquisition method subject to structured queries to arrive at the tridosha levels in a subject.

12 Claims, 4 Drawing Sheets

(58) Field of Classification Search
CPC .............. A61B 5/6824; A61B 5/02438; A61B 2562/0247; A61B 2560/0425; A61B 5/6844

See application file for complete search history.

(56) References Cited

U.S. PATENT DOCUMENTS

| | | | |
|---|---|---|---|
| 6,730,040 B2 * | 5/2004 | Lee .................... | A61B 5/02233 600/500 |
| 6,932,772 B2 * | 8/2005 | Kan .................... | A61B 5/02116 600/485 |
| 8,100,835 B2 | 1/2012 | Baruch | |
| 2002/0065471 A1 | 5/2002 | Amano et al. | |
| 2005/0228298 A1 | 10/2005 | Banet et al. | |
| 2008/0221930 A1 * | 9/2008 | Wekell .................. | H02J 7/0044 705/3 |
| 2010/0152594 A1 * | 6/2010 | Bhat ..................... | A61B 5/6844 600/501 |
| 2015/0031964 A1 * | 1/2015 | Bly ........................ | A61B 5/681 600/301 |
| 2015/0137997 A1 | 5/2015 | Huang | |
| 2015/0164344 A1 | 6/2015 | Jouria | |
| 2015/0257644 A1 | 9/2015 | Coa | |
| 2016/0089042 A1 * | 3/2016 | Saponas ............. | A61B 5/02438 600/407 |

FOREIGN PATENT DOCUMENTS

| | | |
|---|---|---|
| IN | 1675/DEL/2007 | 4/2009 |
| IN | 1892/MUM/2014 A | 6/2014 |
| JP | H07-136139 A | 5/1995 |
| WO | WO-2013/005228 A2 | 1/2013 |

OTHER PUBLICATIONS

International Search Report and Written Opinion dated Sep. 15, 2017 in PCT/IN2017/050217.

* cited by examiner

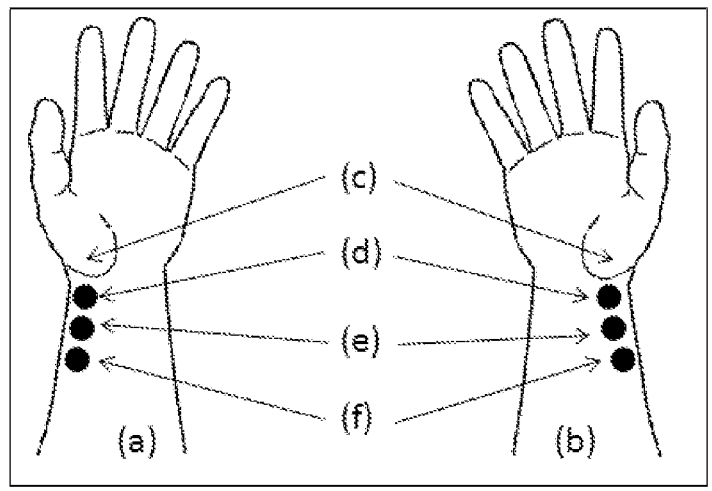
Figure 1.Locations of vata, pitta and kapha pulse on the wrist of a patient
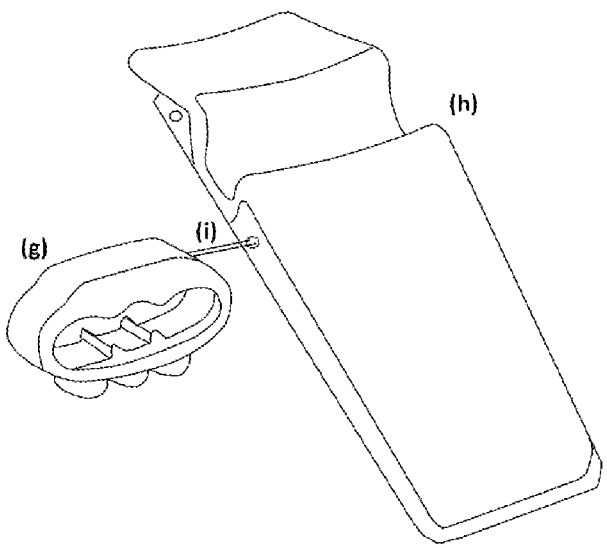
Figure 2.Our complete system with portable unit and base unit

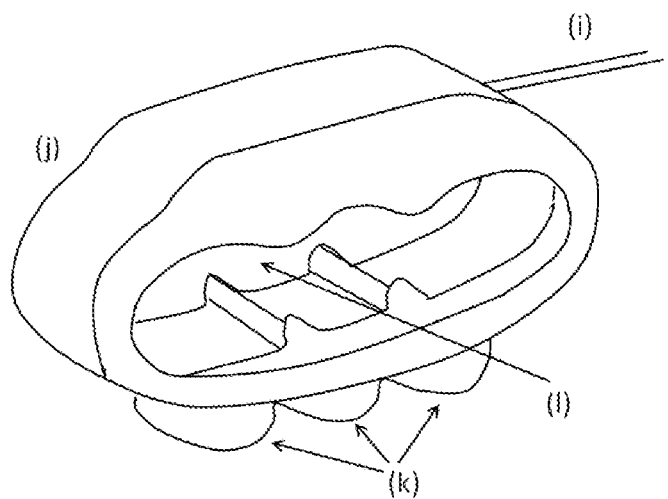
Figure 3. Pulse Signal measuring portable Unit
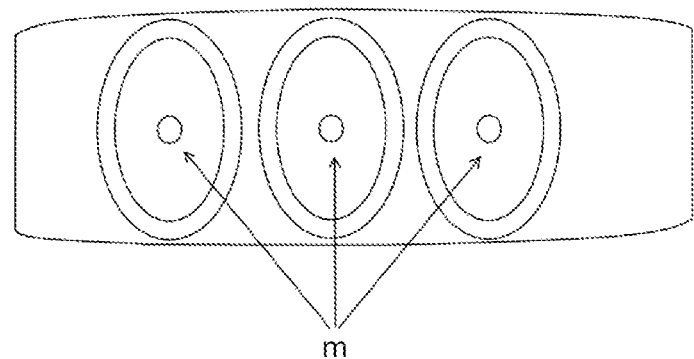
Figure 4. Bottom view of the pulse signal measuring portable unit

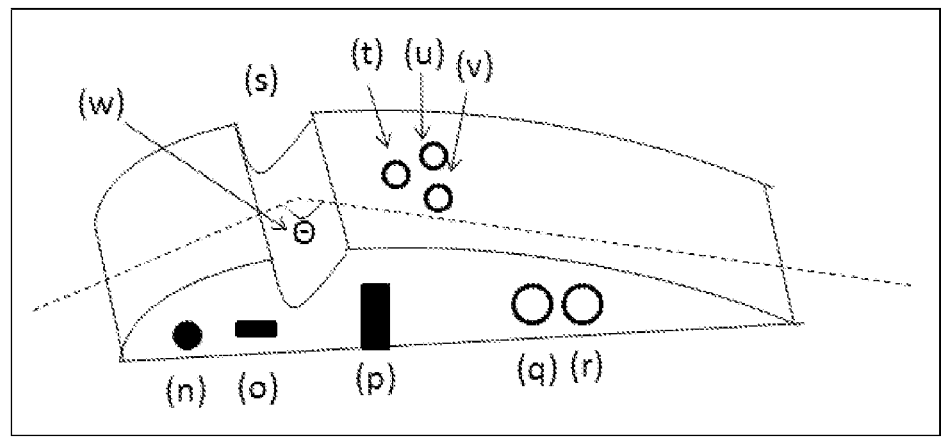
Figure 5. Base Unit
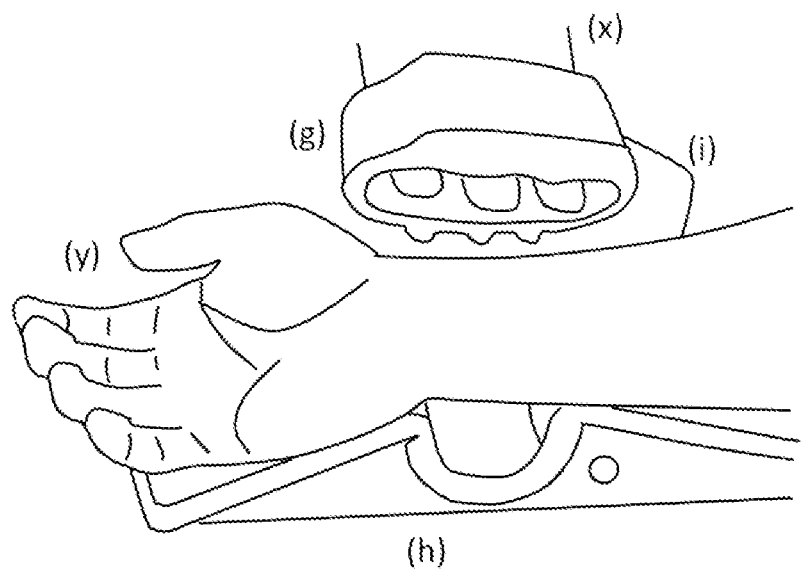
Figure 6. Process of the pulse acquisition method

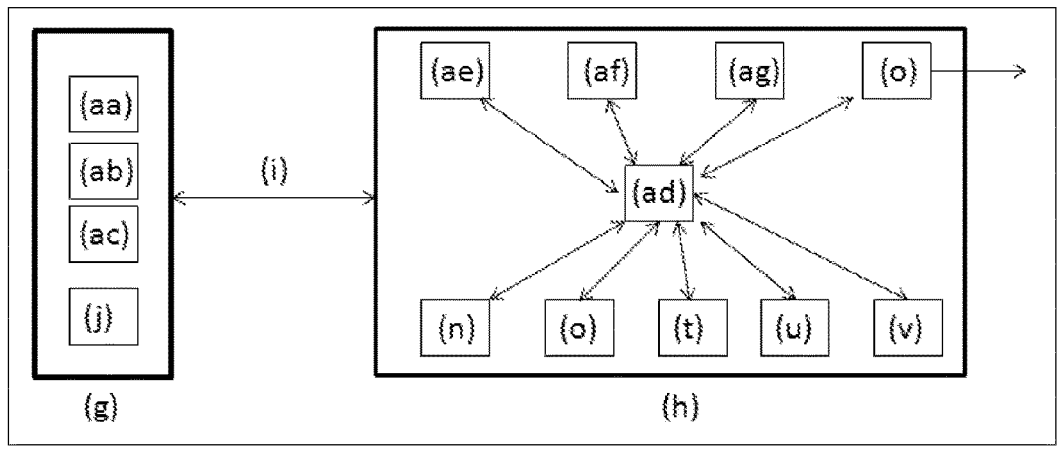
Figure 7. Layout of important components in pulse acquisition system
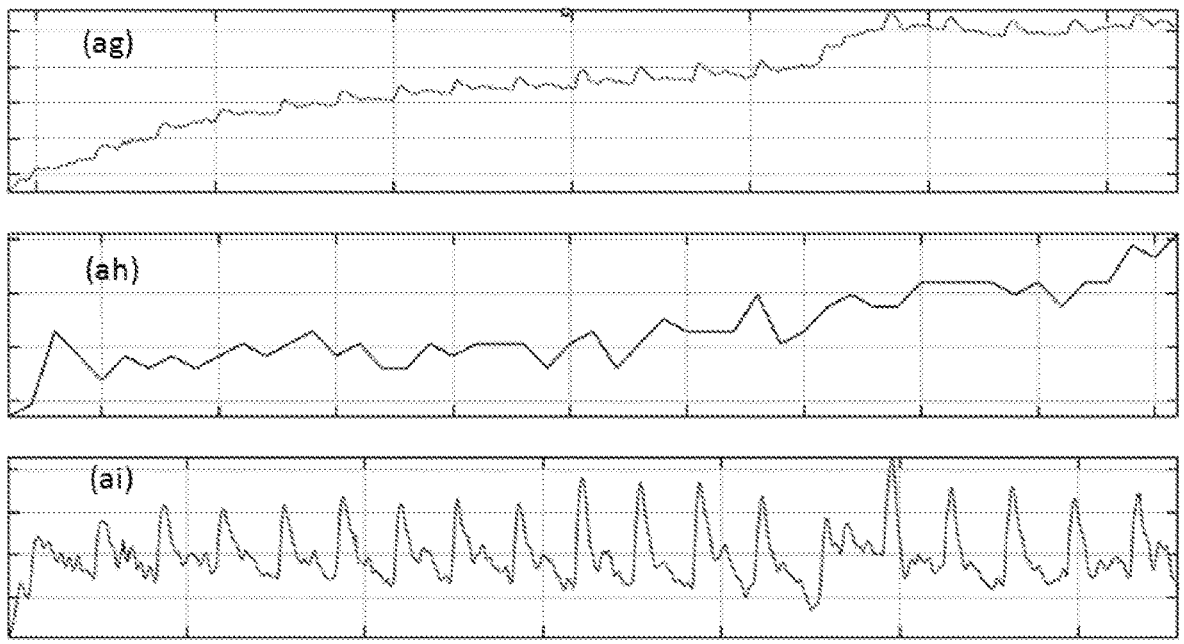
Figure 8. Example of the use of the accelerometer in removing noise from the recorded pulse data.

DEVICE FOR THE DETECTION AND RELIABLE CAPTURING OF THE PULSE CHARACTERISTICS

FIELD OF THE INVENTION

The invention is related to a device to sense the pulse on a wrist of a subject and to arrive at the health status of the said subject. Further, the invention relates to the said device to capture the pulse in real time; analyze the pulse based on time-frequency properties of the pulse signal and Vata, Pitta and Kaphahumors of the subject.

BACKGROUND AND PRIOR ART

Diagnostics and treatment in Ayurveda are based on five basic elements present in the human body in terms of three humors, namely vata (mainly responsible for movements), pitta (mainly responsible for energy) and kapha (mainly responsible for structures). If these three components are present in right proportions, a person is said to be healthy. Pulse-based examination (nadiparikshan) is practised to access the levels of the three dosha (vata, pitta and kapha) in a subject to arrive at the dominance of specific dosha and also imbalance in doshas which are considered to be the root cause of any disorder.

Further, an ayurvedic practitioner uses visual examination and query based interaction with a subject coupled with the assessment of nadiparikshan to finally arrive at the tridosha levels in the subject.

The key challenge in nadiparikshan lies in minimising subjective in feeling of the pulses in a subject as this forms the basic input in the diagnostic and treatment process.

Several attempts have been made in the past to provide devices to accurately measure the pulse and link the pulse data to a subject's visual features and responses to queries.

The closest prior art1675/DEL/2007 relates to a non-invasive device for quantitative detection of arterial nadi pulse waveform and application of advanced machine learning algorithms to identify the pulse patterns. Three diaphragm-based strain gauge elements are to be placed at the exact vata pitta kapha pick up locations and they give equivalent electrical output. The system has a digitizer having an interface with the personal computer at the USB port. This pressure which is small in pressure units is captured in accurate, reproducible and noise-free waveforms to perform accurate diagnosis. A small air gap is introduced between each of the sensing elements and the skin of person. The physiological features such as rhythm, self-similar nature, and chaotic nature present in the pulse are extracted using rigorous machine learning algorithms that are represent various types and sub-types of nadi patterns.

This prior art has the following limitations
i. the recorded pulse data contains noise due to manual movement of the subject's hand or investigator's hand
ii. the rectangular shape of the orifices are not desirable as they may cause distortions in the detection of the pulses
iii. configuration of the sensors and the three orifices located on the neoprene sheet does not simulate the traditional "three finger assessment process" followed in ayurveda.
iv. neoprene sheet used to introduce air gap between the sensor and the skin is neither medically acceptable nor durable
v. the wired USB interface with the computer for storing the pulse signals on the computer is not easily portable There is therefore an unmet need to provide devices for the detection and reliable capturing of the noise free pulse characteristics of a subject at the appropriate locations of the subject's wrist with minimal positional error in a user friendly and standardised manner with minimal reliance on the expertise of the person measuring the pulses, analysing the same and providing a comprehensive diagnostic system involving the captured pulse characteristics, visual features, responses of a subject to structured queries to arrive at the tridosha levels in a subject to enable appropriate course of treatment of the said subject.

Objects of the Inventions

The main object of the invention is to provide a comprehensive cost effective device that sensitively senses and reliably measures the pulse of a subject, analyses the pulses, and correlate them with health indices of the said subject.

Another object of the present invention is to provide flexibility of applying different pressures on the three sensors located in the device to simulate the manner in which pulses are manually felt by a practitioner using his three fingers on the wrist.

Another object of the present invention is to correct for any noise interfering with the pulse data due to manual movement of the subject's hand or investigator's hand.

Another object of the invention is to provide machine learning on the centralized data of collected pulse signals to provide health indices for the diagnostic process.

Another object of the present invention is to provide a device with the option to simultaneously capture pulse signals on both the hands.

Yet another object of the invention is to photograph face of the subject to enable "drushyam" information for the diagnostic process comprising "sparsha, darshana and prashna".

Yet another object of the invention is to record the voice of the subject to include the pitch of the subject simultaneously with recording the pulse signals.

Yet another object of the invention is to record the temperature of the subject simultaneously with recording the pulse signals.

DETAILED DESCRIPTION OF THE INVENTION

The device of the present invention comprises: at least one pulse portable detection unit, a base unit, and a storage system,
wherein
i. the pulse portable detection unit comprises an arrangement of at least three pressure sensors configured to provide an air gap between the sensors and the pulsating substrate to sense the pulse at the vata, pitta and kapha locations on the wrist of a subject, an accelerometer, a controller for controlled acquisition of signals by the said pressure sensors and said accelerometer;
ii. the powered base unit operable connected to the storage unit selected from a communication device, a computer or a cloud based storage.

The apertures associated with the pressure sensors are configured to provide elliptical shaped air gaps between the sensors and the pulsating surface to simulate the manner in which pulses are manually felt by a practitioner using his three fingers on the wrist.

In one of the embodiments, a gap is provided in the base unit for gripping the wrist of the said subject when the reading of the pulse is taken using the portable unit.

In an embodiment, two pulse portable detection units may be operably connected to the powered base unit to simultaneously capture pulse signals on both the hands of a subject.

Single, dual or triple axis accelerometers may be used, though a triple axis accelerometer is preferred. More preferably, the accelerometer is micro electro-mechanical system (MEMS). However, two 2 axis ones mounted at right angles would also serve the purpose.

In an embodiment, a base unit may be configured as a wrist-rester wherein the upper surface has two slopes angled at ⊖ varying from 120° to 179°. The wrist-rester ensures that the wrist of the subject is placed in a range of pre-set angles for recording of the pulse signals.

A temperature sensor for recording the temperature of the subject, a camera to photograph the subject, a microphone to record the voice of the subject may be provided in the pulse portable unit or in the base unit.

The data acquisition and analysis system including display of the results may be suitably integrated into the storage unit and located in storage unit.

FIGS. 1-8 illustrate a specific embodiment of the present invention.

FIG. 1 displays the vata, pitta and kapha locations of the pulse on a subject's two wrists wherein the pulse is sensed using the traditional methodology. In the FIG. 1, (a) indicates left hand of the subject, (b) indicates right hand of the subject, (c) indicates the root of the thumb on the wrist of both the hands just below which the pulse is traditionally sensed, (d) indicates vata location on both the hands, (e) indicates pitta location on both the hands, (f) indicates kapha location on both the hands.

FIG. 2 displays the pulse recording system, wherein (g) indicates pulse signal measuring portable unit, (h) indicates powered base unit, (i) indicates cable connecting the two units.

FIG. 3 displays the pulse signal measuring portable unit, wherein (j) is the accelerometer in the portable unit operably connected to the base unit to sense the spatial movement of the portable unit, (k) indicates the three flexible finger like structures operably connected to the base unit, configured to introduce the air gap between the three pressure sensors and the pulsating substrate being sensed, (l) indicates the space in the portable unit for the investigator to put his or her at least three fingers, (i) indicates the optional cable connecting the portable unit to the base unit.

FIG. 4 indicates the bottom view of the pulse signal measuring portable unit, wherein (m) indicates the three air gaps introduced by the three flexible finger like structures of the portable unit.

FIG. 5 displays the base unit wherein (n) is the power ON/OFF switch, (o) is the micro-usb connector for connecting the base unit to the storage system, (p) are LED indicators for displaying the battery life levels, (q) is an orifice to pass the cable from the portable unit, (r) is an orifice to pass the cable from an optional additional portable unit for other hand of the subject, (s) indicates a gap in the base unit to aid the investigators thumb to gripping the subject's wrist, (t) is an optional temperature sensor for recording temperature of the subject while simultaneously acquiring the pulse signals, (u) is an optional photo camera for taking the photograph of the subject, (v) is an optional microphone for recording the voice of the subject, (w) is the angle ⊖ at which the base unit is curved to raise the pulse sensing locations on the subject's wrist for recording of the pulse signals, wherein the said angle θ may vary from 120° to 179°.

FIG. 6 displays the process of the pulse acquisition method, wherein (x) indicates the three fingers of the investigator located in the portable unit, (g) is the portable unit, (y) is the right hand of the subject, (h) is the base unit, (i) indicates the optional cable connecting the portable unit to the base unit.

FIG. 7 displays an embodiment of the pulse acquisition system wherein (g) is the portable unit, (h) is the base unit, (aa)(ab)(ac) are the three pressure sensors operably connected to the base unit, (j) is the accelerometer operably connected to the base unit, (i) is the cable connecting the base unit with the portable unit, (ad) is the micro-controller to control the preset actions, (ae) is the battery operably connected to all the components, (af) is the BlueTooth operably connected to the storage system, (ag) is the local memory of the base unit for storing the acquired data, (o) is the micro-usb connection operably connected to the storage system, (n) is the ON/OFF switch operably connected to the micro-controller, (p) are the LED indications for battery operably connected to the micro-controller, (t) is an optional temperature sensor, (u) is an optional photo camera, (v) is an optional microphone.

FIG. 8 displays the use of the accelerometer data to remove noise from the recorded pulse data wherein (ag) is a sample pulse data of 20 seconds recorded at vata location, (ah) is the first component of the accelerometer data recorded at the same time of (ag) pulse and (ai) is the resulting de-noised pulse data with signal to noise ratio increased by 7.2 times.

PROCESS OF RECORDING PULSES

The process of recording of the pulse signals using the specific embodiment illustrated in FIGS. 1-8, at the vata, pitta and kaphalocations on the wrist of a subject comprises steps of i. switching ON (n in FIG. 5) the base unit by the investigator and ensuring that there is sufficient power in the system ii. inputting the medical information of the subject in the storage system iii. optionally capturing the subject's photo and storing in the storage system iv. resting the subject's hand on the "wrist-rester"

v. appropriately gripping the subject's wrist by the investigator by placing his thumb in the gap provided in base unit vi. sensing the pulse by the investigator using his three fingers placed in the slot of portable unit and appropriately positioning the portable unit on the wrist's region of the subject using the visualisation provided by a monitor.

vii. acquiring the signals from the pressure sensors, accelerometer, optional temperature sensor in local memory of the base unit and storing the data for further analysis after removal of the portable unit from the subject's wrist viii. optionally recording the subject's voice and storing in the storage system ix. switching OFF the base unit after the data acquisition.

The function of the accelerometer is to monitor the spatial movement of the portable unit containing pressure sensors during data acquisition and discard the pulse data collected due to movement of the wrist of the subject or hand of the investigator. When the accelerometer data values are steady, the simultaneously recorded pulse data does not carry any noise. The accelerometer data is used to produce the de-noised pulse data.

Each pulse signal is computed in terms of depth, intensity, amplitude, frequency, rhythm, length, type, quantity and texture.

The pulse data is analyzed with the help of visual information (darshana) through the face photo, feel information (sparsha) through the pulse signals and questions (prashna) to derive the health indices in terms of Ayurvedic terminologies such as gati, swaroop, prakruti, vikruti, samata, sthoolata, uttanata, gambhirata, sukshmata and bala.

The pulse data is analyzed to derive the health indices in terms of allopathic terminologies such as rate, rhythm, pulse rate variability, topology, cardiovascular parameters and with final remarks of healthy versus unhealthy.

The present system provides technological advancement over all prior art devices as the three pressure sensors in three finger like structures made of medically complied flexible material with elliptical air gap closely truly mimics the traditional method of pulse measurement with three fingers. This arrangement also provides flexibility of applying different pressures on the three pressure sensors located in the system.

Inclusion of the accelerometer provides a means to monitor the spatial location of the portable unit in real time on the wrist of the subject and to discard the data due to data collected during movement of the subject's wrist or the investigator's hand.

The system of the present invention also provides a means of simultaneously acquiring the pulse data from the writs of both the hands of the subject.

Acquisition of temperature, visual aspects, voice of the subject during the pulse data recording and then comprehensively analysing the acquired data provides reliable health indices and diagnosis comprising "sparsha, darshana and prashna".

I claim:

1. A device comprising:
    at least one pulse portable detection unit;
    a base unit; and
    a storage system,
        wherein the at least one pulse portable detection unit comprises at least three pressure sensors and a structure with a surface associated with each pressure sensor, each surface configured to contact a wrist of a subject, a surface of each of the three pressure sensors spaced from the surface of each structure, thereby creating an air gap that extends from the at least three pressure sensors to a pulsating substrate to sense a pulse across the air gap at vata, pitta and kapha locations on the wrist of the subject,
        an accelerometer system configured to monitor a spatial movement of the at least one pulse portable detection unit relative to the base unit, and
        a controller configured to perform controlled acquisition of pulse signals by the at least three pressure sensors and the accelerometer system, wherein accelerometer data from the accelerometer system reduces noise of the pulse signals of the at least pressure sensors, and
    wherein the base unit, when powered, is operably connected to the storage system, the storage system including a communication device, a computer or a cloud based storage.

2. The device as claimed in claim 1, wherein each air gap has an elliptical shape.

3. The device as claimed in claim 1 wherein the accelerometer system is selected from the group consisting of single axis accelerometers or combinations thereof, dual axis accelerometers or combinations thereof, multiple axis accelerometers, or micro-electro-mechanical systems (MEMS) triple axis accelerometer.

4. The device as claimed in claim 1 wherein the base unit has two upper sloped surfaces and a gap is provided between the two upper sloped surfaces for gripping the wrist of the said subject when the reading of the pulse is taken using the portable unit.

5. The device as claimed in claim 1 wherein the base unit includes a wrist-rester wherein an upper surface of the wrist-rester has two slopes angled at an angle varying from 120° to 179° to ensure that the wrist of the subject is placed in a range of pre-set angles for recording of the pulse signals.

6. The device as claimed in 1 wherein a temperature sensor for recording a temperature of the subject, a camera to photograph the subject, a microphone to record the voice of the subject, and combinations thereof are provided in the at least one pulse portable detection unit or in the base unit.

7. The device as claimed in claim 1 wherein a data acquisition and analysis system including display is operably integrated into the storage system.

8. The device as claims in claim 1 wherein the at least one pulse portable detection unit includes two pulse portable detection units that are operably connected to the powered base unit to simultaneously capture pulse signals on both wrists of a subject.

9. The device as claimed in claim 1, wherein the air gap is provided in at least three apertures corresponding to respective ones of the at least three pressure sensors.

10. A device comprising:
    a pulse measuring portable detection unit;
    a base unit; and
    a storage system, wherein
        the pulse measuring portable detection unit comprises a triple axis accelerometer that is operably connected to the base unit to sense a spatial movement of the pulse measuring portable detection unit,
        three flexible finger like structures are operably connected to the base unit, the three flexible finger like structures each have a surface configured to contact a wrist of a subject, a surface of each of the three pressure sensors spaced from the surface of each of the flexible finger like structures to create an air gap, each air gap extending from each of the three pressure sensors to a pulsating substrate being sensed,
        a space is provided in the pulse measuring portable detection unit for receiving at least three fingers of an investigator,
        a cable connects the pulse measuring portable detection unit to the bae unit, and
        the base unit is curved at an angle to raise pulse sensing locations on a wrist of the subject for recording of pulse signals, wherein the angle varies from 120° to 179°, and
        the base unit includes at least one of a temperature sensor to record a temperature of the subject, a camera to photograph the subject, and a microphone to record a voice of the subject at a time of measuring the pulse signals of the subject, wherein the triple axis accelerator is configured to provide accelerometer data to reduce noise of the pulse signals of the three pressure sensors.

11. The device as claimed in claim 10, wherein the air gaps are provided in three apertures corresponding to respective ones of the three flexible finger like structures.

12. A method of recording pulse signals at vata, pitta, and kapha locations on a wrist of a subject using the device of claim 1, the method comprising steps of:
- switching on the base unit;
- inputting medical information of the subject in the storage system;
- capturing at least one photo of the subject and storing the at least one photo in the storage system;
- causing at least one wrist of the subject to rest on a wrist-rester;
- gripping the at least one wrist of the subject by placing a thumb of an investigator in a gap provided in the base unit;
- sensing the pulse using three fingers of the investigator placed in a slot of the pulse portable detection unit and positioning the pulse portable detection unit on a region of the at least one wrist of the subject;
- acquiring data including the pulse signals from the three pressure sensors, the accelerometer system, a temperature sensor in local memory of the base unit and storing the data for further analysis;
- recording a voice of the subject and storing the voice of the subject in the storage system,
- switching OFF the base unit after the data acquisition; and
- reducing noise of pulse signals of the three pressure sensors using accelerometer data.

* * * * *